(12) United States Patent
Oshinski et al.

(10) Patent No.: US 12,350,478 B2
(45) Date of Patent: Jul. 8, 2025

(54) DETECTION SYSTEM FOR SYRINGE ASSEMBLY

(71) Applicant: Becton, Dickinson and Company, Franklin Lakes, NJ (US)

(72) Inventors: Matthew Oshinski, Oak Ridge, NJ (US); Ashley Rachel Rothenberg, Morris Plains, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 948 days.

(21) Appl. No.: 17/600,695

(22) PCT Filed: Apr. 1, 2020

(86) PCT No.: PCT/US2020/026111
§ 371 (c)(1),
(2) Date: Oct. 1, 2021

(87) PCT Pub. No.: WO2020/205929
PCT Pub. Date: Oct. 8, 2020

(65) Prior Publication Data
US 2022/0184321 A1 Jun. 16, 2022

Related U.S. Application Data

(60) Provisional application No. 62/828,025, filed on Apr. 2, 2019.

(51) Int. Cl.
*A61M 5/31* (2006.01)
*A61M 5/24* (2006.01)
*A61M 5/315* (2006.01)

(52) U.S. Cl.
CPC .......... *A61M 5/31568* (2013.01); *A61M 5/24* (2013.01); *A61M 5/31511* (2013.01);
(Continued)

(58) Field of Classification Search
CPC ................ A61M 5/31568; A61M 5/24; A61M 5/31511; A61M 2205/3306; A61M 2205/3317; A61M 2205/33; A61M 5/31
See application file for complete search history.

(56) References Cited

U.S. PATENT DOCUMENTS 5,375,596 A 12/1994 Twiss et al.
5,882,338 A 3/1999 Gray
(Continued)

FOREIGN PATENT DOCUMENTS

CN 103714615 A 4/2014
CN 104021411 A 9/2014
(Continued)

*Primary Examiner* — Nathan R Price
*Assistant Examiner* — Amina Ishrat
(74) *Attorney, Agent, or Firm* — The Webb Law Firm

(57) ABSTRACT

Detection systems for a syringe assembly that provide precision in monitoring the amount of fluid contained within the syringe barrel, detecting motion of the plunger within the syringe barrel, detecting the position of the plunger within the syringe barrel, and/or monitoring the volume received within or delivered by the syringe assembly are disclosed. A detection system of the present disclosure allows a sensor in communication with a portion of a plunger assembly to sense the motion of a plunger rod relative to a syringe barrel and thereby volume received within or delivered by the syringe by reading gradations having an identifier directly as the plunger rod with sensor moves past each respective gradation with identifier.

20 Claims, 4 Drawing Sheets

(52) U.S. Cl.
CPC .............. *A61M 2205/3306* (2013.01); *A61M 2205/3317* (2013.01)

(56) References Cited

U.S. PATENT DOCUMENTS

| | | | |
|---|---|---|---|
| 6,019,745 A | 2/2000 | Gray | |
| 6,310,475 B1 | 10/2001 | Kawase et al. | |
| 7,115,113 B2 | 10/2006 | Evans et al. | |
| 7,498,563 B2 | 3/2009 | Mandro et al. | |
| 8,075,490 B2 | 12/2011 | Löfgren et al. | |
| 9,976,551 B2 | 5/2018 | Blomquist | |
| 10,737,061 B2 | 8/2020 | Parmar | |
| 2004/0024368 A1* | 2/2004 | Broselow | A61M 5/31525 604/207 |
| 2004/0186437 A1 | 9/2004 | Frenette et al. | |
| 2006/0088199 A1 | 4/2006 | Shizuka et al. | |
| 2007/0060820 A1* | 3/2007 | Lofgren | A61B 5/0215 600/481 |
| 2014/0249410 A1* | 9/2014 | Uber, III | A61M 5/20 604/246 |
| 2016/0206806 A1* | 7/2016 | Wright | A61M 5/24 |
| 2016/0213834 A1 | 7/2016 | Brady et al. | |
| 2016/0259913 A1 | 9/2016 | Yu et al. | |
| 2017/0119962 A1 | 5/2017 | Fazi, Jr. | |
| 2020/0188598 A1* | 6/2020 | Schabbach | A61M 5/31568 |

FOREIGN PATENT DOCUMENTS

| | | | |
|---|---|---|---|
| CN | 109221081 A | 1/2019 | |
| EP | 2674181 A2 | 12/2013 | |
| FR | 3023725 A3 * | 1/2016 | ............ A61J 1/1418 |
| JP | H8509402 A | 10/1996 | |
| JP | 2000105847 A | 4/2000 | |
| JP | 2004334144 A | 11/2004 | |
| JP | 201243361 A | 3/2012 | |
| WO | 2013004843 A1 | 1/2013 | |
| WO | 2015001008 A1 | 1/2015 | |
| WO | 2015038494 A1 | 3/2015 | |
| WO | 2016071912 A1 | 5/2016 | |
| WO | 2016140853 A1 | 9/2016 | |

* cited by examiner

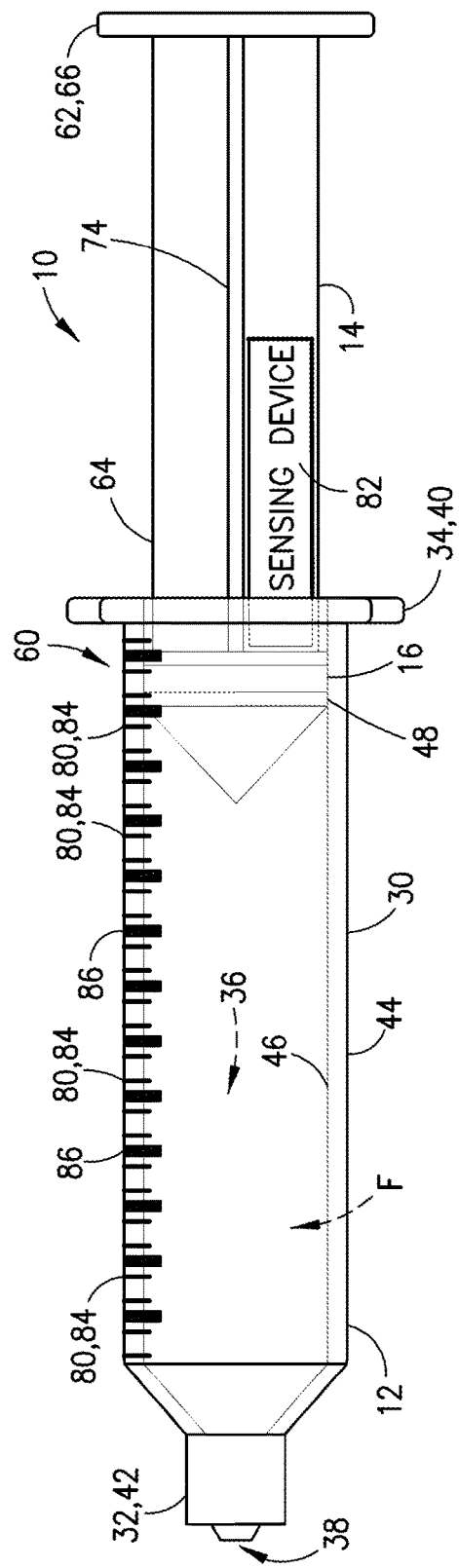
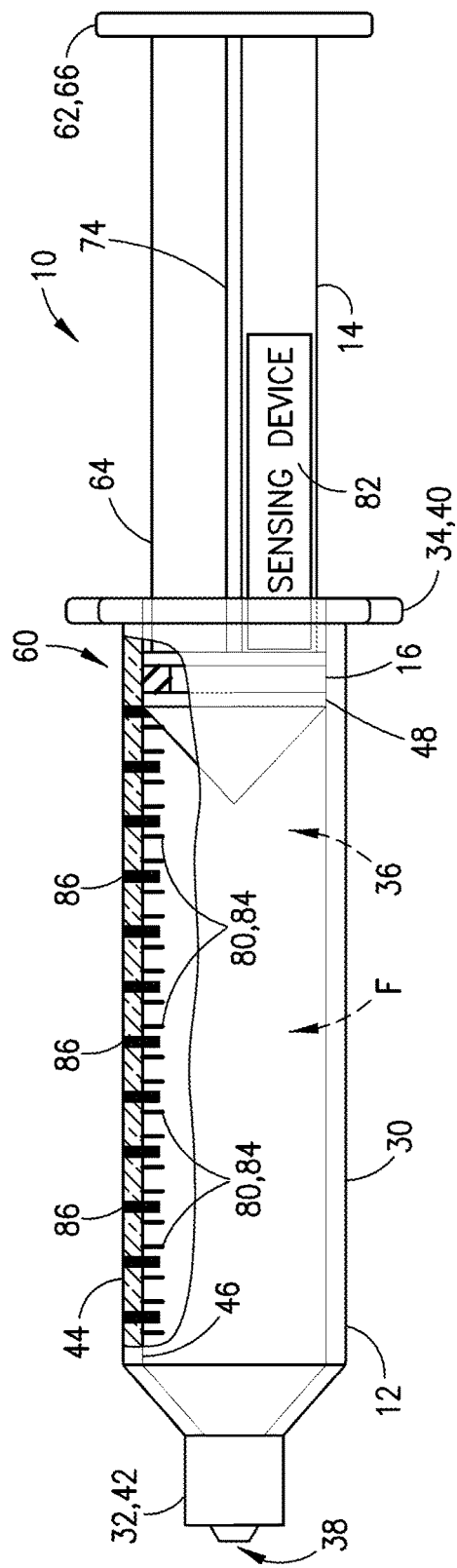

DETECTION SYSTEM FOR SYRINGE ASSEMBLY

CROSS-REFERENCE TO RELATED APPLICATIONS

The present application is the United States national phase of International Application No. PCT/US2020/026111 filed Apr. 1, 2020, and claims priority to U.S. Provisional Application Ser. No. 62/828,025, filed Apr. 2, 2019, entitled "Detection System for Syringe Assembly", the entire disclosures of which are hereby incorporated by reference.

BACKGROUND OF THE INVENTION

1. Field of the Disclosure

The present disclosure relates generally to a detection system for a syringe assembly. More particularly, the present disclosure relates to an identifier in a first portion of the syringe assembly and a sensor in a second portion of the syringe assembly to detect motion of the syringe assembly and monitor the volume received within or delivered by the syringe assembly.

2. Description of the Related Art

Syringe assemblies, and in particular hypodermic syringes, are well known in the medical field for dispensing fluids, such as medications. A conventional syringe typically includes a syringe barrel with an opening at one end and a plunger mechanism disposed through the opposite end. The plunger mechanism typically includes a plunger rod extending through the barrel, with a plunger head or stopper disposed at the end of the plunger rod within the syringe barrel, and with a finger flange at the other end of the plunger rod extending out of the syringe barrel. In use, the plunger rod is retracted through the syringe barrel to aspirate or fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the syringe barrel for attachment with a fluid line of a patient. Upon the user applying a force to depress the plunger rod and stopper through the syringe barrel towards the front end of the syringe barrel, the contents of the syringe are thereby forced out of the syringe barrel through the opening at the front end for delivery to the patient. Such an operation is well known in the medical field, and medical practitioners have become well accustomed to the use of such common fluid delivery procedures through standard syringes.

A syringe barrel may include markings, such as gradations located on a sidewall of the syringe barrel, for providing an indication as to the level or amount of fluid contained within an interior chamber of the syringe barrel. However, there is a need for more precise systems for monitoring the amount of fluid contained within the syringe barrel, detecting motion of the plunger within the syringe barrel, detecting the position of the plunger within the syringe barrel, and/or monitoring the volume received within or delivered by the syringe assembly.

SUMMARY OF THE INVENTION

The present disclosure provides detection systems for a syringe assembly that provide precision in monitoring the amount of fluid contained within the syringe barrel, detecting motion of the plunger within the syringe barrel, detecting the position of the plunger within the syringe barrel, and/or monitoring the volume received within or delivered by the syringe assembly.

A detection system of the present disclosure allows a sensor in communication with a portion of a plunger assembly to sense the motion of a plunger rod relative to a syringe barrel and thereby volume received within or delivered by the syringe by reading gradations having an identifier directly as the plunger rod with sensor moves past each respective gradation with identifier.

In accordance with an embodiment of the present invention, a syringe assembly includes a syringe barrel having a first end, a second end, and a sidewall extending therebetween and defining an interior; a plurality of gradations located on a portion of the sidewall, the plurality of gradations each including an identifier; a plunger assembly having a first end, a second end, and a plunger stopper portion slidably disposed within the interior of the syringe barrel, the plunger stopper portion sized relative to the interior of the syringe barrel to provide sealing engagement with the sidewall of the syringe barrel; and a sensor in communication with a portion of the plunger assembly, wherein the sensor detects the identifier.

In one configuration, the sensor is positioned within a portion of the plunger assembly. In another configuration, the sensor is mounted on a portion of the plunger assembly. In yet another configuration, the sensor is formed as part of a portion of the plunger assembly. In one configuration, the gradations are located on an inner portion of the sidewall. In another configuration, the syringe assembly includes human readable gradations on an outer portion of the sidewall. In yet another configuration, the gradations are located on an outer portion of the sidewall. In one configuration, the syringe assembly includes human readable gradations on an outer portion of the sidewall. In another configuration, the identifiers are part of the human readable gradations. In yet another configuration, the identifiers are transparent. In one configuration, the identifier is magnetic. In another configuration, the sensor is a magnetic sensor. In yet another configuration, the identifier is IR ink. In one configuration, the sensor is an optical sensor. In another configuration, the identifier is UV ink.

In accordance with another embodiment of the present invention, a syringe assembly includes a syringe barrel having a first end, a second end, and a sidewall extending therebetween and defining an interior; a plurality of gradations located on a portion of the sidewall, the plurality of gradations each including an identifier; a plunger rod having a first end and a second end; a stopper engaged with the second end of the plunger rod and slidably disposed within the interior of the syringe barrel, the stopper sized relative to the interior of the syringe barrel to provide sealing engagement with the sidewall of the syringe barrel; and a sensor that detects the identifier.

In one configuration, the sensor is positioned within a portion of the plunger rod. In another configuration, the sensor is mounted on a portion of the plunger rod. In yet another configuration, the sensor is formed as part of a portion of the plunger rod. In one configuration, the sensor is positioned within a portion of the stopper. In another configuration, the sensor is mounted on a portion of the stopper. In yet another configuration, the sensor is formed as part of a portion of the stopper. In one configuration, the gradations are located on an inner portion of the sidewall. In another configuration, the syringe assembly includes human readable gradations on an outer portion of the sidewall. In yet another configuration, the gradations are located on an outer portion of the sidewall. In one configuration, the syringe assembly includes human readable gradations on an outer portion of the sidewall. In another configuration, the identifiers are part of the human readable gradations. In yet another configuration, the identifiers are transparent. In one configuration, the identifier is magnetic. In another configuration, the sensor is a magnetic sensor. In yet another configuration, the identifier is IR ink. In one configuration, the sensor is an optical sensor. In another configuration, the identifier is UV ink.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 4 is an assembled view of a syringe assembly in a second position with a detection system in accordance with another embodiment of the present invention.

FIG. 5 is an assembled view of a syringe assembly in a second position with a detection system in accordance with another embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
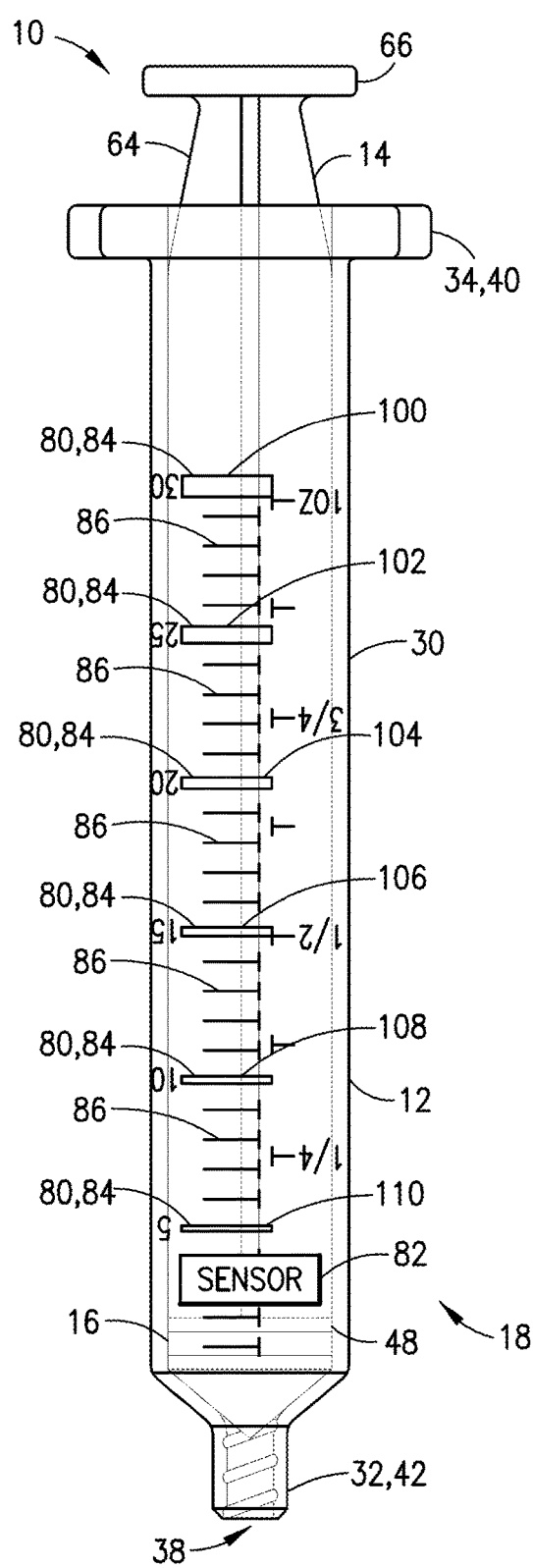
FIG. 1 is an assembled, perspective view of a syringe assembly in a first position with a detection system in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

The present disclosure provides detection systems for a fluid container, such as a syringe assembly, IV bag, pen injector, autoinjector, and the like that provide precision in monitoring the amount of fluid contained within the container, detecting motion of a plunger within the container, and/or monitoring the volume received within or delivered by the fluid container. In one embodiment, the present disclosure provide a detection system for a syringe barrel, detecting motion of the plunger within the syringe barrel, detecting the position of the plunger within the syringe barrel, and/or monitoring the volume received within or delivered by the syringe assembly.

A detection system of the present disclosure allows a sensor in communication with a portion of a plunger assembly to sense the motion of a plunger rod relative to a syringe barrel and thereby volume received within or delivered by the syringe by reading gradations having an identifier directly as the plunger rod with sensor moves past each respective gradation with identifier.

Figure 6:
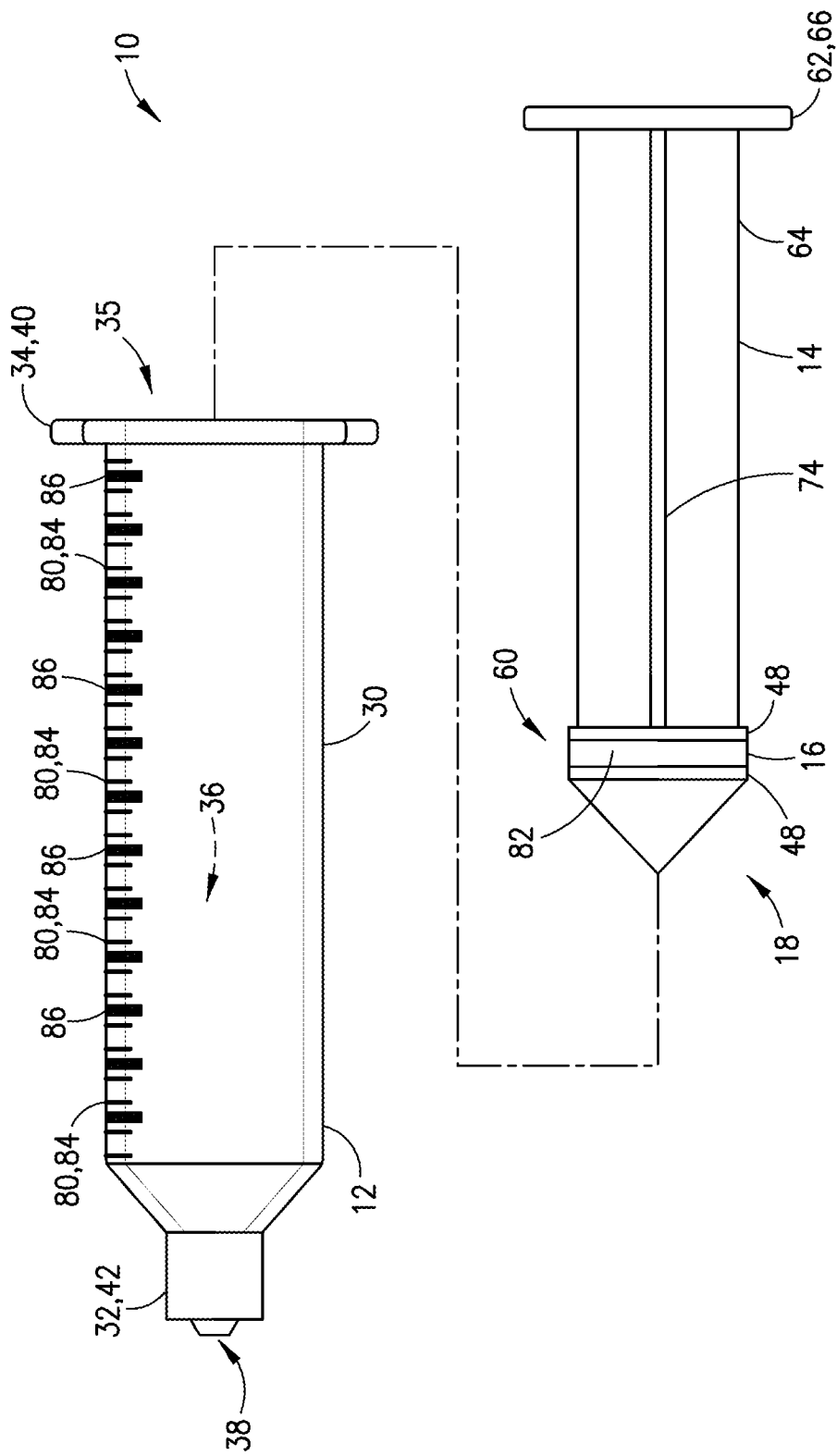
FIG. 6 is an exploded, perspective view of a syringe assembly with a detection system in accordance with another embodiment of the present invention.

Referring to FIGS. 1-6, a fluid container, such as a syringe assembly 10 having a detection system 18 includes a syringe barrel 12, a plunger rod or plunger assembly 14, and a stopper 16. Syringe assembly 10 may be adapted for dispensing and delivery of a fluid and/or collection of a fluid. For example, syringe assembly 10 may be used for injection or infusion of fluid such as a medication into a patient. Syringe assembly 10 is contemplated for use in connection with a needle, such as by connecting syringe assembly 10 to a separate needle assembly (not shown), or alternatively for connection with an intravenous (IV) connection assembly (not shown). It can be appreciated that the present disclosure can be used with any type of syringe assembly. These types of syringes include traditional pre-filled syringe assemblies, metered dose syringes, aspiration syringes for withdrawing fluid from a patient or medication from a container, and the like. It is also contemplated herein that the fluid container may also be an IV bag, pen injector, autoinjector, patch-style injector, or the like Referring to FIGS. 1-6, syringe barrel 12 generally includes a barrel body or sidewall 30 extending between a first or distal end 32 and a second or proximal end 34. The sidewall 30 includes an external surface or outer portion 44 and an internal surface or inner portion 46. Proximal end 34 of syringe barrel 12 defines a proximal opening 35 (FIG. 6). Sidewall 30 defines an elongate aperture or interior chamber 36 of syringe barrel 12. In one embodiment, interior chamber 36 may span the extent of syringe barrel 12 so that syringe barrel 12 is cannulated along its entire length. In one embodiment, syringe barrel 12 may be in the general form of an elongated cylindrical barrel as is known in the art in the general shape of a hypodermic syringe. In alternative embodiments, syringe barrel 12 may be in other forms for containing a fluid for delivery, such as in the general form of an elongated rectangular barrel, for example. Syringe barrel 12 may be formed of glass, or may be injection molded from thermoplastic material such as polypropylene and polyethylene according to techniques known to those of ordinary skill in the art, though it is to be appreciated that syringe barrel 12 may be made from other suitable materials and according to other applicable techniques. In certain configurations, syringe barrel 12 may include an outwardly extending flange 40 about at least a portion of proximal end 34. Flange 40 may be configured for easy grasping by a medical practitioner.

Distal end 32 of syringe barrel 12 includes an outlet opening 38 which is in fluid communication with chamber 36. Outlet opening 38 may be sized and adapted for engagement with a separate device, such as a needle assembly or IV connection assembly and, therefore, may include a mechanism for such engagement as is conventionally known. For example, distal end 32 may include a generally-tapered luer tip 42 for engagement with an optional separate tapered luer structure of such a separate device for attachment therewith (not shown). In one configuration, both the tapered luer tip 42 and the separate tapered luer structure may be provided with syringe assembly 10. In such a configuration, the separate tapered luer structure may be fitted with an attachment mechanism, such as a threaded engagement, for corresponding engagement with a separate device (not shown). In another configuration, tapered luer tip 42 may be provided for direct engagement with a separate device (not shown). In addition, a mechanism for locking engagement therebetween may also be provided with at least one of tapered luer tip 42 and/or the separate tapered luer structure, such as a luer collar or luer lock including interior threads. Such luer connections and luer locking mechanisms are well known in the art.

Proximal end 34 of syringe barrel 12 is generally open-ended, but is intended to be closed off to the external environment. For example, in one embodiment, the proximal end 34 of syringe barrel 12 defines a proximal opening 35 (FIG. 6).

Syringe assembly 10 may be useful as a pre-filled syringe, and, therefore, may be provided for end use with a fluid, such as a medication or drug, contained within interior chamber 36 of syringe barrel 12, pre-filled by the manufacturer. In this manner, syringe assembly 10 can be manufactured, pre-filled with a medication, and sterilized for delivery, storage, and use by the end user, without the need for the end user to fill the syringe with medication from a separate vial prior to use. In such an embodiment, syringe assembly 10 may include a protective cap disposed over outlet opening 38 at distal end 32 of syringe barrel 12 to seal a fluid F, such as a medication, within interior chamber 36 of syringe barrel 12. The syringe assembly 10 may also include additional packaging and sealing portions to enclose the syringe assembly 10 to seal and protect the fluid F, such as a medication, within interior chamber 36 of syringe barrel 12.

Syringe assembly 10 may also be used to fill syringe barrel 12 with a medication from a separate vial prior to use. For example, syringe assembly 10 may be used with non-preloaded medication kits such as a diabetes therapy kit or other medication kits.

Referring to FIGS. 1-6, in one embodiment, syringe assembly 10 includes stopper 16 which is moveably or slidably disposed within interior chamber 36, and in sealing contact with the internal surface of sidewall 30 of syringe barrel 12. Stopper 16 is sized relative to the interior of syringe barrel 12 to provide sealing engagement with the interior surface 46 of sidewall 30 of syringe barrel 12. In a pre-filled syringe assembly, stopper 16 also provides a first seal to prevent liquid or medication from leaking out of syringe barrel 12. Additionally, in one embodiment, stopper 16 may include one or more annular ribs 48 extending around the periphery of stopper 16 to increase the sealing engagement between stopper 16 and the interior surface 46 of sidewall 30 of syringe barrel 12. In alternate embodiments, a singular O-ring or a plurality of O-rings may be circumferentially disposed about stopper 16 to increase the sealing engagement with the interior surface of sidewall 30.

Referring to FIGS. 1-6, syringe assembly 10 further includes plunger rod 14 which provides a mechanism for dispensing fluid contained within interior chamber 36 of syringe barrel 12 through outlet opening 38.

Plunger rod 14 is adapted for advancing stopper 16. In one embodiment, plunger rod 14 is sized for movement within interior chamber 36 of syringe barrel 12 and generally includes a first or distal end 60 engageable with a portion of stopper 16, a second or proximal end 62 generally opposite first end 60, a plunger rod body 64 extending between first end 60 and second end 62, and a flange 66 disposed adjacent second end 62.

Referring to FIGS. 1-6, in one embodiment, plunger rod 14 includes stabilizing ribs 74 extending between distal end 60 and proximal end 62 of plunger rod 14. In one embodiment, stabilizing ribs 74 extend along a longitudinal axis of plunger rod 14. In other embodiments, stabilizing ribs 74 may include one or more annular ribs extending around the periphery of plunger rod 14. Stabilizing ribs 74 provide a means to stabilize plunger rod 14 within syringe barrel 12 and guide plunger rod 14 during movement within interior chamber 36 of syringe barrel 12.

Referring to FIGS. 1-6, plunger rod 14 includes a first end 60 that is engageable with a portion of stopper 16. In one embodiment, plunger rod 14 and stopper 16 may include engagement portions for securing plunger rod 14 to stopper 16. For example, the engagement portions may include corresponding threaded portions for securing plunger rod 14 to stopper 16. In other embodiments, the engagement portions may include a snap fit mechanism, a press-fit mechanism, a ball detent, locking tabs, spring loaded locking mechanism, latch, adhesive, or other similar mechanism. In another embodiment, plunger rod 14 and stopper 16 may be co-formed such as by co-extrusion. Plunger rod 14 is locked to stopper 16, i.e., significant relative movement between plunger rod 14 and stopper 16 is prevented and movement of plunger rod 14 can be transferred to stopper 16 to slide stopper 16 between positions within syringe barrel 12. In other embodiments, plunger rod 14 and stopper 16 may be integrally formed as a plunger assembly.

All of the components of syringe assembly 10 may be constructed of any known material, and are desirably constructed of medical-grade polymers.

The present disclosure provides detection systems 18 for a syringe assembly 10 that provide precision in monitoring the amount of fluid contained within the syringe barrel 12, detecting motion of the plunger 14 within the syringe barrel 12, detecting the position of the plunger 14 within the syringe barrel 12, and/or monitoring the volume received within or delivered by the syringe assembly 10. Referring to FIGS. 1-6, in one embodiment, the detection system 18 of the syringe assembly 10 includes an identifier 80 that is part of a first portion of the syringe assembly 10 and a sensor or sensing device 82 that is part of a second portion of the syringe assembly 10. A detection system 18 of the present disclosure allows a sensor 82 in communication with a portion of a syringe assembly 10 and/or plunger assembly 14 to sense the motion of a plunger 14 relative to a syringe barrel 12 and thereby volume received within or delivered by the syringe 10 by reading gradations 84 having an identifier 80 directly as the plunger rod 14 with sensor 82 moves past each respective gradation 84 with identifier 80.

In one embodiment, syringe barrel 12 include a first set of markings or gradations 84 located on a portion of sidewall 30 of syringe barrel 12 for providing an indication as to the level or amount of fluid contained within interior chamber 36 of syringe barrel 12 and for providing indications of the additional information described herein. Such markings 84 may be provided on an external surface or outer portion 44 of sidewall 30, an internal surface or inner portion 46 of sidewall 30, or integrally formed or otherwise within sidewall 30 of syringe barrel 12. In other embodiments, alternatively, or in addition thereto, the markings 84 may also provide a description of the contents of the syringe or other identifying information as may be known in the art, such as maximum and/or minimum fill lines.

The plurality of markings or gradations 84 may each include an identifier 80 that is detectable by a sensor 82. For example, in one embodiment, the identifier 80 includes gradation markings 84 that are printed on the syringe barrel 12 using magnetic ink. In such an embodiment, a portion of the syringe assembly 10 or the plunger rod 14 includes a sensor 82, e.g., a magnetic sensing sensor, that is able to detect each of the identifiers 80, i.e., the sensor 82 detects the magnetic ink forming the gradation markings 84. In this manner, the identifier 80 and the sensor 82 form a detection system 18 that provides precision in monitoring the amount of fluid contained within the syringe barrel, detecting motion of the plunger within the syringe barrel, detecting the position of the plunger within the syringe barrel, and/or monitoring the volume delivered by the syringe assembly.

Referring to FIG. 1, in one embodiment, the syringe barrel 12 may include a first identifier 100 including a gradation marking 84 that is printed on the syringe barrel 12 using magnetic ink, a second identifier 102 including a gradation marking 84 that is printed on the syringe barrel 12 using magnetic ink, a third identifier 104 including a gradation marking 84 that is printed on the syringe barrel 12 using magnetic ink, a fourth identifier 106 including a gradation marking 84 that is printed on the syringe barrel 12 using magnetic ink, a fifth identifier 108 including a gradation marking 84 that is printed on the syringe barrel 12 using magnetic ink, and a sixth identifier 110 including a gradation marking 84 that is printed on the syringe barrel 12 using magnetic ink. In some embodiments, additional identifiers 80 including a gradation marking 84 that is printed on the syringe barrel 12 using magnetic ink may be included on the syringe barrel 12 for a particular application. In other embodiments, less identifiers 80 including a gradation marking 84 that is printed on the syringe barrel 12 using magnetic ink may be included on the syringe barrel 12 for other applications. It is envisioned that a detection system 18 of the present disclosure can be adapted to include any number of identifiers 80 in any particular patterns for a variety of different applications.

Figure 3:
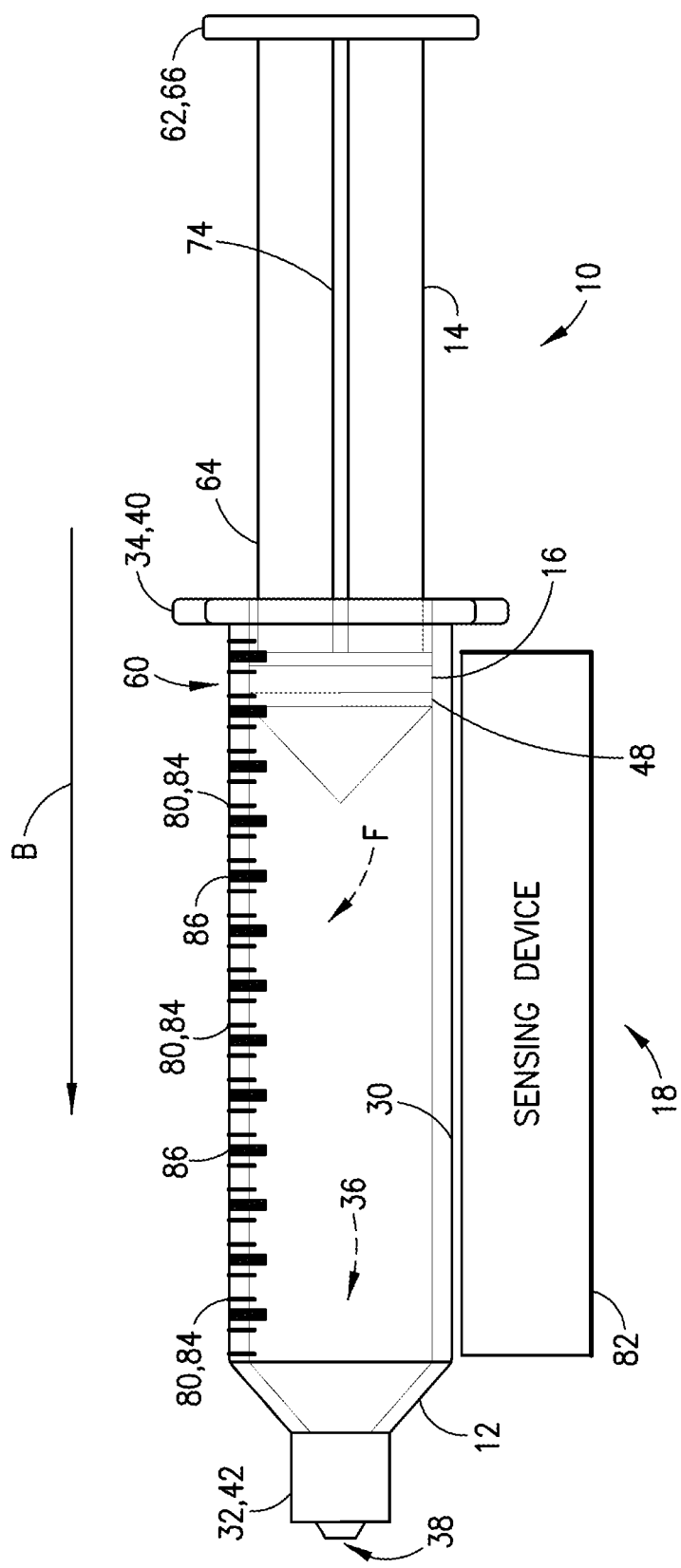
FIG. 3 is an assembled view of a syringe assembly in a second position with a detection system in accordance with another embodiment of the present invention.

In this manner, as the plunger rod 14 moves from a fully retracted position, as shown in FIG. 3, toward the distal end 32 of syringe barrel 12 in a direction generally along arrow B (FIG. 3), the sensor 82 is able to determine movement along the syringe barrel 12 by detecting the printed pattern of the magnetic ink in the identifiers 100, 102, 104, 106, 108, 110. Furthermore, in this manner, the detection system 18 of the present disclosure also provides precision in monitoring the amount of fluid contained within the syringe barrel, detecting motion of the plunger within the syringe barrel, detecting the position of the plunger within the syringe barrel, and/or monitoring the volume delivered by the syringe assembly.

In other words, the detection system 18 of the present disclosure allows a sensor 82 in communication with a portion of the syringe assembly 10 or the plunger rod 14 to sense the motion of the plunger rod 14 relative to the syringe barrel 12 and thereby volume received within or delivered by the syringe 10 by reading the gradations 84 having an identifier 80 directly as the plunger rod 14 with sensor 82 moves past each respective gradation 84 with identifier 80.

Referring to FIG. 1, in one embodiment, the line weight of each of the identifiers 100, 102, 104, 106, 108, 110 is varied so that the strength of the signal detected by the sensor 82 provides information about the absolute position of the plunger rod 14 relative to the syringe barrel 12.

As described above, in one embodiment, the detection system 18 of the present disclosure includes a magnetic sensor 82 paired with magnetic ink identifiers 80. In other embodiments, the detection system 18 of the present disclosure may include other pairings of a sensor 82 with an identifier 80.

Figure 2:
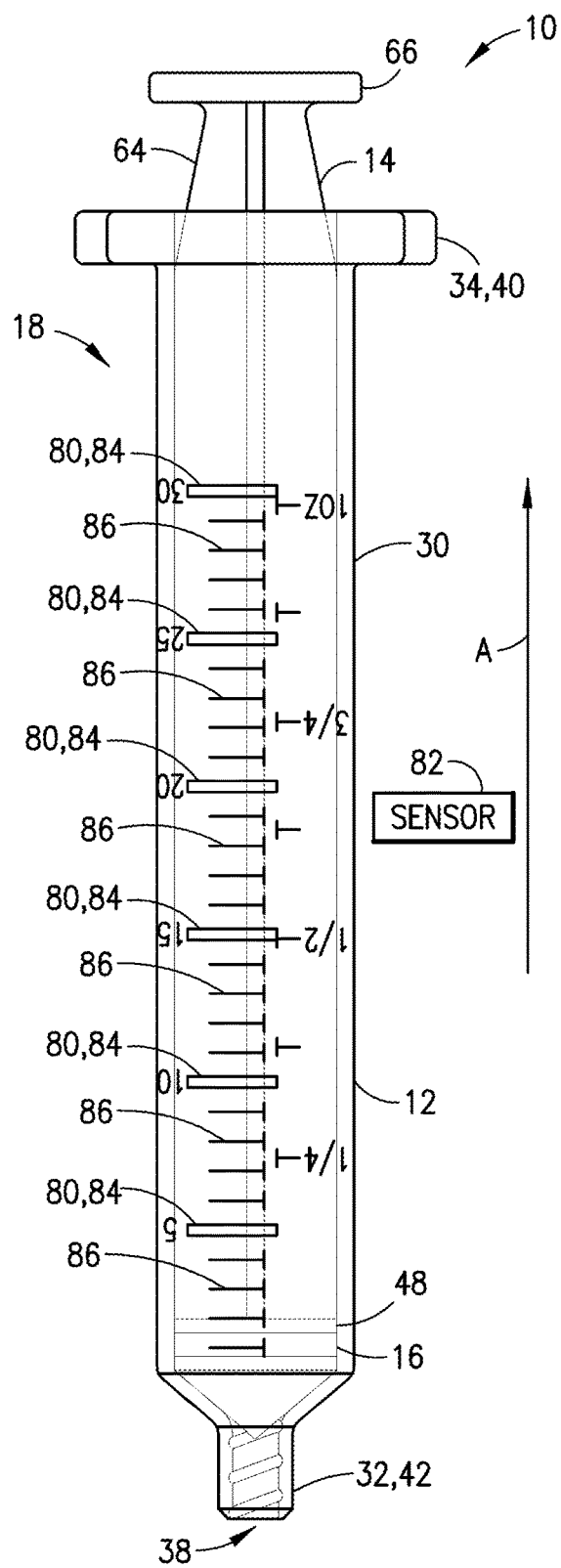
FIG. 2 is an assembled, perspective view of a syringe assembly in a first position with a detection system in accordance with another embodiment of the present invention.

For example, referring to FIG. 2, in another embodiment, the identifier 80 includes gradation markings 84 that are printed on the syringe barrel 12 using UV reflective ink. In such an embodiment, a portion of the syringe assembly 10 or the plunger rod 14 includes a sensor 82 that is able to detect each of the identifiers 80, i.e., the sensor 82 detects the UV reflective ink forming the gradation markings 84. In this manner, the identifier 80 and the sensor 82 form a detection system 18 that provides precision in monitoring the amount of fluid contained within the syringe barrel, detecting motion of the plunger within the syringe barrel, detecting the position of the plunger within the syringe barrel, and/or monitoring the volume delivered by the syringe assembly. In such an embodiment, the sensor 82 is able to more readily read information on the syringe gradations by enhanced signals that are provided to the sensor 82 by the UV reflective ink. In such an embodiment, a UV or other non-visible optically active ink could be used to enhance the functionality of the sensor 82 and signals generated. It is also contemplated herein that the identifier 80 could also include other information which would otherwise be printed on a label applied to the device, such as, the kind of fluid container and/or contents of the fluid container. By including this kind of information within the identifier 80, information which would otherwise be printed on a label foes not inhibit or block a user's normal use of the syringe's visible gradations, contents or volume.

In another embodiment, the identifier 80 includes gradation markings 84 that are printed on the syringe barrel 12 using IR ink. In such an embodiment, a portion of the plunger rod 14 includes a sensor 82, e.g., an optical sensor, that is able to detect each of the identifiers 80, i.e., the sensor 82 detects the IR ink forming the gradation markings 84. In this manner, the identifier 80 and the sensor 82 form a detection system 18 that provides precision in monitoring the amount of fluid contained within the syringe barrel, detecting motion of the plunger within the syringe barrel, detecting the position of the plunger within the syringe barrel, and/or monitoring the volume delivered by the syringe assembly.

Referring to FIGS. 4 and 5, in some embodiments, the sensor 82 is positioned within a portion of the plunger rod 14, or stopper 16, to detect the identifiers 80 forming the gradation markings 84 and determine the position of the plunger rod 14 based on this detection. In other embodiments, the sensor 82 may be in communication with other portions of the plunger rod 14 and/or the stopper 16. For example, in other embodiments, it is envisioned that the sensor 82 is mounted on a portion of the plunger rod 14, the sensor 82 is formed as part of a portion of the plunger rod 14, the sensor 82 is positioned within a portion of the stopper 16, the sensor 82 is mounted on a portion of the stopper 16, or the sensor 82 is formed as part of a portion of the stopper 16. For example, referring to FIGS. 2 and 3, in some embodiments, the sensor or sensing device 82 may be in communication with a portion of the plunger assembly 14 and disposed outside of the syringe barrel 12. In some embodiments, referring to FIG. 6, the sensor 82 may be part of the stopper 16.

In one embodiment, the syringe barrel 12 may include a first set of markings or gradations 84 that have the identifiers 80 therein and a second set of markings or gradations 86 that have human readable gradations.

For example, referring to FIG. 5, in one exemplary embodiment, the first set of markings or gradations 84 that have the identifiers 80 are located on an inner portion 46 of the sidewall 30 of the syringe barrel 12 and the second set of markings or gradations 86 that have human readable gradations are located on an outer portion 44 of the sidewall 30 of the syringe barrel 12. In this manner, the detection system 18 of the present disclosure prints the identifiers 80 on an opposing side of the syringe barrel 12, e.g., the inner portion 46, from the human readable gradations 86 that are located on the outer portion 44. Such a configuration keeps the outer portion 44 of the syringe barrel 12 free for user observation while utilizing the inner portion 46 of the syringe barrel 12 for detection and sensing capabilities. This configuration also provides the added benefit of the human readable gradations 86, located on the outer portion 44 of the syringe barrel 12, being accessible by normally intended line of sight. Furthermore, in one embodiment, the identifiers 80 on a portion of the syringe barrel 12 are transparent to prevent confusion to a user while reading the human readable gradations 86.

Referring to FIGS. 3 and 4, in another exemplary embodiment, the first set of markings or gradations 84 that have the identifiers 80 are located on an outer portion 44 of the sidewall 30 of the syringe barrel 12 and the second set of markings or gradations 86 that have human readable gradations are located on an outer portion 44 of the sidewall 30 of the syringe barrel 12. In one such embodiment, the identifiers 80 may be part of the human readable gradations 86. For example, the identifiers 80 may be added to a portion of each of the human readable gradations 86. In another such embodiment, the identifiers 80 may be separate from the human readable gradations 86.

As described above, in some embodiments, plunger rod 14 and stopper 16 may be integrally formed as a plunger assembly. The integrally formed plunger assembly 14 includes the first end 60, the second end 62, and a plunger stopper portion, e.g., a stopper 16 that is integrally formed with a plunger rod 14, which is slidably disposed within the interior 36 of the syringe barrel 12. The plunger stopper portion is sized relative to the interior 36 of the syringe barrel 12 to provide sealing engagement with the sidewall 30 of the syringe barrel 12. In such embodiments, a sensor 82 of the detection system 18 of the present disclosure is in communication with a portion of the plunger assembly 14. For example, it is envisioned that the sensor 82 is positioned within a portion of the plunger assembly 14, the sensor 82 is mounted on a portion of the plunger assembly 14, or the sensor 82 is formed as part of a portion of the plunger assembly 14. Referring to FIGS. 2 and 3, in some embodiments, the sensor or sensing device 82 may be in communication with a portion of the plunger assembly 14 and disposed outside of the syringe barrel 12. In such embodiments, a variety of different configurations of the detection system 18 of the present disclosure are envisioned as described in detail above.

Referring now to FIGS. 1-6, the use of syringe assembly 10 with detection system 18 of the present disclosure to fill syringe barrel 12 with medication from a separate vial prior to use will now be described. With syringe assembly 10 in the position shown in FIGS. 1 and 2 and with a needle assembly locked to distal end 32 of syringe barrel 12 and placed in communication with a vial containing fluid, when it is desired to aspirate or pull the fluid, such as a medication, into chamber 36 of syringe barrel 12, a user moves plunger rod 14 in a direction generally along arrow A (FIG. 2) until the desired amount of the fluid is pulled into chamber 36 of syringe barrel 12. In this manner, movement of stopper 16 via plunger rod 14 in the direction generally along arrow A (FIG. 2) creates a vacuum inside chamber 36 of syringe barrel 12. As the user moves stopper 16 via plunger rod 14 from the position shown in FIG. 2 towards the position shown in FIG. 3, the user actively increases the volume within chamber 36 of syringe barrel 12. Because the stopper 16 is sized relative to syringe barrel 12 to provide sealing engagement with the interior wall 46 of syringe barrel 12, as described above, and because the needle assembly locked to distal end 32 of syringe barrel 12 is placed in a vial containing fluid, no air can enter into chamber 36 of syringe barrel 12 and, thus, the same number of air molecules are located within chamber 36 as the user actively increases the volume within chamber 36. This decreases the pressure in chamber 36 of syringe barrel 12 relative to the air pressure outside of syringe barrel 12. Therefore, a vacuum, i.e., a space of lower air pressure, is created to pull the fluid, such as a medication, into chamber 36 of syringe barrel 12.

The detection system 18 of the present disclosure allows a sensor 82 in communication with a portion of the syringe assembly 10 or the plunger rod 14 to sense the motion of the plunger rod 14 relative to the syringe barrel 12 as a user moves plunger rod 14 in a direction generally along arrow A (FIG. 2) until the desired amount of the fluid is pulled into chamber 36 of syringe barrel 12 by reading the gradations 84 having an identifier 80 directly as the plunger rod 14 with sensor 82 moves past each respective gradation 84 with identifier 80. In this manner, the detection system 18 of the present disclosure provides precision in monitoring the amount of fluid contained within the syringe barrel, detecting motion of the plunger within the syringe barrel, and/or detecting the position of the plunger within the syringe barrel.

The syringe assembly 10 with detection system 18 of the present disclosure may also be used in a pre-filled syringe assembly and/or an injectable syringe assembly. In this manner, the need for the user to fill the device prior to injection is eliminated, thereby saving time and maintaining consistent volumes for delivery.

Referring to FIG. 3, the use of syringe assembly 10 with detection system 18 of the present disclosure to expel a fluid, such as a medication, contained within chamber 36 of syringe barrel 12 will now be described. Referring to FIG. 3, a fluid F is contained within chamber 36 of syringe barrel 12. In one embodiment, fluid F is contained within chamber 36 between stopper 16 and distal end 32 of syringe barrel 12. A user can then attach tip 42 of syringe barrel 12 to a separate needle assembly or IV connection assembly and lockingly engage the needle assembly or IV connection assembly to tip 42 of syringe barrel 12 in a known manner. Prior to dispensing any medication, any air trapped within chamber 36 of syringe barrel 12 can be expelled in a known manner.

When it is desired to expel or deliver the medication contained within syringe barrel 12, syringe assembly 10 is grasped with the user's thumb on flange 66 of plunger rod 14 and with the user's fingers extending around flange 40 of syringe barrel 12. In this manner, syringe assembly 10 is grasped by a user in a well-known and well recognized manner Next, the user effects a squeezing movement between the thumb on flange 66 of plunger rod 14 and four fingers grasping flange 40 of syringe barrel 12, thereby causing stopper 16 via plunger rod 14 to move in a direction generally along arrow B (FIG. 3). In this manner, movement of stopper 16 via plunger rod 14 in the direction generally along arrow B forces the fluid F contained within chamber 36 of syringe barrel 12 to be forced out outlet opening 38. The fluid can be expelled from syringe barrel 12 through outlet opening 38 into a separate needle assembly or IV assembly and into the patient.

Advantageously, using the detection system 18 of the present disclosure, as the plunger rod 14 moves from a fully retracted position, as shown in FIG. 3, toward the distal end 32 of syringe barrel 12 in a direction generally along arrow B (FIG. 3), the sensor 82 is able to determine movement along the syringe barrel by detecting the printed pattern of the magnetic ink in the identifiers 100, 102, 104, 106, 108, 110 (FIG. 1). Furthermore, in this manner, the detection system 18 of the present disclosure also provides precision in monitoring the amount of fluid contained within the syringe barrel, detecting motion of the plunger within the syringe barrel, detecting the position of the plunger within the syringe barrel, and/or monitoring the volume delivered by the syringe assembly.

In other words, the detection system 18 of the present disclosure allows a sensor 82 in communication with a portion of the plunger rod 14 to sense the motion of the plunger rod 14 relative to the syringe barrel 12 and thereby volume delivered by the syringe 10 by reading the gradations 84 having an identifier 80 directly as the plunger rod 14 with sensor 82 moves past each respective gradation 84 with identifier 80.

In one exemplary embodiment, the detection systems of the present disclosure integrates the addition of an additive that functions as an identifier to a human readable ink on a portion of a syringe barrel to provide precision in monitoring the amount of fluid contained within the syringe barrel, detecting motion of the plunger within the syringe barrel, detecting the position of the plunger within the syringe barrel, and/or monitoring the volume received within or delivered by the syringe assembly. In another exemplary embodiment, the detection systems of the present disclosure introduce an additive that functions as an identifier to an opposite side of a syringe barrel from a human readable ink to keep an outer portion with the human readable ink free for observation while utilizing an inner portion with the identifier for detection and sensing capabilities.

Furthermore, the application of the detection system and syringe identification by the detection of gradations of the present disclosure can include mechanical advantages to external operations and functions through co-operating devices. Ink additives can act as a signature to a method of detection for mechanical specific adaptation. Ink additives can also act as an assisting mechanism for sensing administration as a stopper of a plunger assembly creates a greater contrast as the stopper and/or plunger assembly moves past each respective gradations with identifier. Ink additives can also include sensing-assistive properties to improve functions including the following: (1) optical, e.g., optical array, optical scanner or linear scanner, sparsely populated array with pattern matching; (2) RF based antenna; (3) IR/Ultrasonic TOF; (4) inductive encoder or LVDT; (5) interferometry; (6) magnetic encoder, digital image correlation or darkfield laser tracking, as in an optical mouse; (7) capacitive; or (8) resistance based. Additionally, use of functional ink allows for the printing of a pattern on a syringe that provides a means of absolute position sensing via having a unique pattern or distance between the markings of the ink to allow for a specific variation on the signal received by the sensor.

The addition of magnetic particles to syringe gradations, or other optical elements, creates a greater contrast between the plunger rod and the syringe gradients for enhanced viewing by a sensor. Additionally, the addition of magnetic particles to syringe gradations, or other optical elements, aids a sensor mounted on the plunger rod itself to sense the motion of the plunger rod and thereby the volume delivered by the syringe by reading the syringe markings directly as it moves past them. A sensor of the detection system may also be manufactured as part of a plunger assembly, e.g., as an addition or modification to the stopper. The sensor type and markings could be of any of a number of different technologies.

Additional applications of the inks and detection systems of the present disclosure may be utilized in other means of fluid transfer in a medical environment. The inks could be added to other medical containers such as pen injectors or IV bags for tracking consumption. It could also be applied in diagnostic applications for sample tracking and processing, and in robotic applications of filling or transferring fluids such as drug compounding.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A fluid container assembly, comprising:
   a container barrel having a first end, a second end, and a sidewall extending therebetween and defining an interior;
   a plurality of gradations located on a portion of the sidewall, the plurality of gradations each including an identifier, wherein the identifier is formed of magnetic ink, and wherein a line weight of each identifier differs from a line weight of each of the other identifiers of the plurality of gradations;
   a plunger assembly having a first end, a second end, and a plunger stopper portion slidably disposed within the interior of the container barrel, the plunger stopper portion sized relative to the interior of the container barrel to provide sealing engagement with the sidewall of the container barrel; and
   a sensor in communication with a portion of the plunger assembly, wherein the sensor detects the line weight of each identifier to determine a position of the plunger assembly relative to the container barrel, and wherein the sensor comprises a magnetic sensor.

2. The fluid container assembly of claim 1, wherein the fluid container is a syringe and the container barrel is a syringe barrel.

3. The fluid container assembly of claim 1, wherein the sensor is positioned within a portion of the plunger assembly.

4. The fluid container assembly of claim 1, wherein the sensor is mounted on a portion of the plunger assembly.

5. The fluid container assembly of claim 1, wherein the sensor is formed as part of a portion of the plunger assembly.

6. The fluid container assembly of claim 1, wherein the gradations are located on an inner portion of the sidewall.

7. The fluid container assembly of claim 6, further comprising human readable gradations on an outer portion of the sidewall.

8. The fluid container assembly of claim 1, wherein the gradations are located on an outer portion of the sidewall.

9. The fluid container assembly of claim 8, wherein the gradations are human readable.

10. The fluid container assembly of claim 1, wherein the identifiers are transparent.

11. A syringe assembly, comprising:
- a syringe barrel having a first end, a second end, and a sidewall extending therebetween and defining an interior;
- a plurality of gradations located on a portion of the sidewall, the plurality of gradations each including an identifier, wherein the identifier is formed of magnetic ink, and wherein a line weight of each identifier differs from a line weight of each of the other identifiers of the plurality of gradations;
- a plunger rod having a first end and a second end;
- a stopper engaged with the second end of the plunger rod and slidably disposed within the interior of the syringe barrel, the stopper sized relative to the interior of the syringe barrel to provide sealing engagement with the sidewall of the syringe barrel; and
- a sensor that detects the line weight of each identifier to provide information about a position of the plunger assembly relative to the container barrel, wherein the sensor is a magnetic sensor.

12. The syringe assembly of claim 11, wherein the sensor is positioned within a portion of the plunger rod.

13. The syringe assembly of claim 11, wherein the sensor is mounted on a portion of the plunger rod.

14. The syringe assembly of claim 11, wherein the sensor is formed as part of a portion of the plunger rod.

15. The syringe assembly of claim 11, wherein the sensor is positioned within a portion of the stopper.

16. The syringe assembly of claim 11, wherein the sensor is mounted on a portion of the stopper.

17. The syringe assembly of claim 11, wherein the sensor is formed as part of a portion of the stopper.

18. The syringe assembly of claim 11, wherein the gradations are located on an inner portion of the sidewall.

19. The syringe assembly of claim 11, wherein the gradations are located on an outer portion of the sidewall.

20. The syringe assembly of claim 11, wherein the identifiers are transparent.

* * * * *